United States Patent
Plagnol et al.

(10) Patent No.: US 12,378,595 B2
(45) Date of Patent: *Aug. 5, 2025

(54) METHOD FOR THE ANALYSIS OF MINIMAL RESIDUAL DISEASE

(71) Applicant: Inivata Ltd., Cambridge (GB)

(72) Inventors: Vincent Plagnol, Cambridge (GB); Tim Forshew, Stevenage (GB); Samuel Woodhouse, Cambridge (GB); Andrew Lawson, Waltham Cross (GB); Matthew Smith, Cambridge (GB)

(73) Assignee: INIVATA LTD, Cambridge (GB)

( * ) Notice: Subject to any disclaimer, the term of this patent is extended or adjusted under 35 U.S.C. 154(b) by 113 days.

This patent is subject to a terminal disclaimer.

(21) Appl. No.: 18/367,944

(22) Filed: Sep. 13, 2023

(65) Prior Publication Data

US 2024/0110224 A1 Apr. 4, 2024

Related U.S. Application Data

(63) Continuation of application No. 18/123,235, filed on Mar. 17, 2023, now Pat. No. 11,788,116, which is a continuation of application No. 18/088,402, filed on Dec. 23, 2022, now abandoned, which is a continuation of application No. 16/749,858, filed on Jan. 22, 2020, now Pat. No. 11,566,274, which is a continuation of application No. PCT/IB2019/056625, filed on Aug. 2, 2019.

(60) Provisional application No. 62/716,082, filed on Aug. 8, 2018.

(51) Int. Cl.
| | | |
|---|---|---|
| C12P 19/34 | (2006.01) | |
| C12Q 1/6806 | (2018.01) | |
| G06F 17/18 | (2006.01) | |
| G16B 50/00 | (2019.01) | |

(52) U.S. Cl.
CPC ........... *C12Q 1/6806* (2013.01); *G06F 17/18* (2013.01); *G16B 50/00* (2019.02); *C12Q 2600/158* (2013.01); *C12Q 2600/16* (2013.01)

(58) Field of Classification Search
CPC .................................................. C12Q 1/6869
See application file for complete search history.

(56) References Cited

U.S. PATENT DOCUMENTS

| | | |
|---|---|---|
| 7,727,720 B2 | 6/2010 | Dhallan |
| 9,145,587 B2 | 9/2015 | Morley |
| 10,262,755 B2 | 4/2019 | Babiarz et al. |
| 10,329,627 B1 | 6/2019 | Beeler et al. |
| 10,597,709 B2 | 3/2020 | Zimmermann et al. |
| 10,640,819 B2 | 5/2020 | Rosenfeld et al. |
| 10,889,858 B2 | 1/2021 | Talasaz et al. |
| 2004/0086892 A1 | 5/2004 | Crothers et al. |
| 2006/0263789 A1 | 11/2006 | Kincaid |
| 2007/0020640 A1 | 1/2007 | McCloskey et al. |
| 2008/0003142 A1 | 1/2008 | Link et al. |
| 2011/0230372 A1 | 9/2011 | Willman et al. |
| 2012/0208706 A1 | 8/2012 | Downing et al. |
| 2014/0288116 A1 | 9/2014 | Bandla et al. |
| 2014/0296081 A1 | 10/2014 | Diehn et al. |
| 2016/0275240 A1 | 9/2016 | Huelga et al. |
| 2016/0362748 A1 | 12/2016 | Mongan et al. |
| 2017/0204455 A1 | 7/2017 | Rosenfeld et al. |
| 2017/0283854 A1 | 10/2017 | Dervinis et al. |
| 2018/0002747 A1 | 1/2018 | Druley et al. |
| 2020/0263260 A1 | 8/2020 | Chudova |
| 2020/0347140 A1 | 11/2020 | Kragh et al. |
| 2021/0015787 A1 | 1/2021 | Nezami |
| 2021/0125683 A1 | 4/2021 | Zhou et al. |

FOREIGN PATENT DOCUMENTS

| | | |
|---|---|---|
| CN | 106282356 A | 1/2017 |
| CN | 106834275 A | 6/2017 |
| CN | 107002123 A | 8/2017 |
| WO | 2007024798 A2 | 3/2007 |
| WO | 2008144841 A1 | 12/2008 |
| WO | 2011140187 A2 | 11/2011 |
| WO | 2012142611 A2 | 10/2012 |
| WO | 2013036929 A1 | 3/2013 |
| WO | 2014118377 A2 | 8/2014 |
| WO | 2015075196 A1 | 5/2015 |
| WO | 2016009224 A1 | 1/2016 |
| WO | 2017091865 A1 | 6/2017 |
| WO | WO 2018/083467 A1 | 5/2018 |

OTHER PUBLICATIONS

Murtaza et al., Multifocal clonal evolution characterized using circulating tumour DNA in a case of metastatic breast cancer, Nature Communications, Nov. 4, 2015, 6:8460, pp. 1-6.

Narayan et al., Ultrasensitive measurement of hotspot mutations in tumor DNA in blood using error-suppressed multiplexed deep sequencing, Cancer Research, 72(14), Jul. 15, 2012, pp. 3492-3498.

Nik-Zainal et al., The Life History of 21 Breast Cancers, Cell 149, May 25, 2012, pp. 994-1007.

Ohtani et al., Immune cell expression of TGFβ1 in cancer with lymphoid stroma: dendritic cell and regulatory T cell contact, Virchows Archiv, 472, Mar. 28, 2018, pp. 1021-1028.

Olsson et al., Serial monitoring of circulating tumor DNA in patients with primary breast cancer for detection of occult metastatic disease, EMBO Molecular Medicine, vol. 7, No. 8, 2015, pp. 1034-1047.

Ottesen et al., Microfluidic Digital PCR for Multigene Analysis of Individual Environmental Bacteria, Science 314, No. 5804, Reprint, 2006, pp. 1-35.

(Continued)

*Primary Examiner* — Kenneth R Horlick
(74) *Attorney, Agent, or Firm* — James S. Keddie; Bozicevic, Field & Francis LLP

(57) ABSTRACT

Provided herein is a method for the analysis of minimal residual disease, the method comprising obtaining multiple pairs of primers, performing a targeted multiplex amplification using the multiple pairs of primers to produce amplicons, sequencing the amplicons or an amplification product thereof, thereby generating sequence reads, calculating a score based on the minority of sequences containing identified sequence variations, and using the calculated score to determine the presence or absence of minimal residual disease in the patient.

20 Claims, 2 Drawing Sheets

(56) References Cited

OTHER PUBLICATIONS

Parameswaran et al., A pyrosequencing-tailored nucleotide barcode design unveils opportunities for large-scale sample multiplexing, Nucleic Acids Research, vol. 35, No. 19, e130, Oct. 11, 2007, pp. 1-9.

Paweletz et al., Bias-Corrected Targeted Next-Generation Sequencing for Rapid, Multiplexed Detection of Actionable Alterations in Cell-Free DNA from Advanced Lung Cancer Patients, Clinical Cancer Research, 22(4), Oct. 12, 2015, pp. 915-923.

Qiu et al., DNA Sequence-Based "Bar Codes" for Tracking the Origins of Expressed Sequence Tags from a Maize cDNA Library Constructed Using Multiple mRNA Sources, Plant Physiology, vol. 133, Oct. 2003, pp. 475-481.

Riely, What, When, and How of Biomarker Testing in Non-Small Cell Lung Cancer, Journal of the National Comprehensive Cancer Network, vol. 15, No. 5.5, May 2017, pp. 686-688.

Salk et al., Enhancing the accuracy of next-generation sequencing for detecting rare and subclonal mutations, Nat Rev Genet, 19(5), May 2018, pp. 1-38.

Shaw et al., Genomic analysis of circulating cell-free DNA infers breast cancer dormancy, Genome Research, 2012, pp. 220-231.

Shendure et al., Advanced Sequencing Technologies: Methods and Goals, Nature Reviews, Genetics, vol. 5, May 2004, pp. 335-344.

Shokralla et al., Next-generation DNA barcoding: using next-generation sequencing to enhance and accelerate DNA barcode capture from single specimens, Molecular Ecology Resources, 14, Jan. 17, 2014, pp. 892-901.

Sidransky, Emerging Molecular Markers of Cancer, Nature Reviews, Cancer, vol. 2, Mar. 2002, pp. 210-219.

Skoulidis et al., STK11/LKB1 Mutations and PD-1 Inhibitor Resistance in KRAS-Mutant Lung Adenocarcinoma, Cancer Discovery, 8(7), Jul. 2018, pp. 1-26.

Soda et al., A Prospective PCR-Based Screening for the EML4-ALK Oncogene in Non-Small Cell Lung Cancer, Clinical Cancer Research, 18(20), Oct. 15, 2012, pp. 5682-5690.

Strickler et al., Genomic Landscape of Cell-Free DNA in Patients with Colorectal Cancer, Cancer Discovery, Feb. 2018, pp. 164-174.

Thierry et al., Clinical utility of circulating DNA analysis for rapid detection of actionable mutations to select metastatic colorectal patients for anti-EGFR treatment, Annals of Oncology, vol. 28, Issue 9, 2017, pp. 2149-2159.

Untergasser et al., Primer3-new capabilities and interfaces, Nucleic Acids Research, vol. 40, No. 15, e115, Jun. 22, 2012, pp. 1-12.

Wapner et al., Expanding the scope of noninvasive prenatal testing: detection of fetal microdeletion syndromes, American Journal of Obstetrics & Gynecology, 212:332, Mar. 2015, pp. e1-e9.

Warren et al., Transcription factor profiling in individual hematopoietic progenitors by digital RT-PCR, PNAS, vol. 103, No. 47, Nov. 21, 2006, p. 17807-17812.

Wilke et al., Prognostic significance of regulatory T cells in tumor, International Journal of Cancer, 127, 2010, pp. 748-758.

Wills et al., Role of liquid biopsies in colorectal cancer, Current Problems in Cancer, vol. 42, Issue 6, Nov. 2018, pp. 593-600.

Xia et al., Statistical analysis of mutant allele frequency level of circulating cell-free DNA and blood cells in healthy individuals, Scientific Reports, 7: 7526, Aug. 8, 2017, pp. 1-7.

Forshew et al., "Noninvasive Identification and Monitoring of Cancer Mutations by Targeted Deep Sequencing of Plasma DNA", Cancer Genomics, May 2012, 4(136): 1-12.

Kou et al., "Benefits and Challenges with Applying Unique Molecular Identifiers in Next Generation Sequencing to Detect Low Frequency Mutations", PLoS One, 2016, 11(1): e0146638, 15 pages.

Deleye et al., "Performance of four modern whole genome amplification methods for copy No. variant detection in single cells", Scientific Reports, 2017, 7: 3422, 9 pages.

Abbosh et al., Phylogenetic ctDNA analysis depicts early-stage lung cancer evolution, Nature, vol. 545, May 25, 2017, 22 pages.

Au et al., BAMClipper: removing primers from alignments to minimize falsenegative mutations in amplicon next-generation sequencing, Nature, Scientific Reports, 7: 1567, May 8, 2017, pp. 1-7.

Bardelli et al., Liquid Biopsies, What We Do Not Know (Yet), Cancer Cell Perspective, 31, Feb. 13, 2017, pp. 172-179.

Beadling et al., A Multiplexed Amplicon Approach for Detecting Gene Fusions by Next-Generation Sequencing, The Journal of Molecular Diagnostics, vol. 18, No. 2, Mar. 2016, pp. 165-175.

Beerenwinkel et al., Cancer Evolution: Mathematical Models and Computational Inference, Systematic Biology, vol. 64(1), 2015, pp. e1-e25.

Beije et al., Somatic mutation detection using various targeted detection assays in paired samples of circulating tumor DNA, primary tumor and metastases from patients undergoing resection of colorectal liver metastases, Molecular Oncology 10, Oct. 10, 2016, pp. 1575-1584.

Bernabe et al., What do we need to make circulating tumour DNA (ctDNA) a routine diagnostic test in lung cancer?, European Journal of Cancer 81, Jun. 10, 2017, pp. 66-73.

Blomquist et al., Targeted RNA-Sequencing with Competitive Multiplex-PCR Amplicon Libraries, PLOS One, vol. 8, Issue 11, Nov. 2013, e79120. pp. 1-14.

Cabel et al., Circulating tumor DNA changes for early monitoring of anti-PD1 immunotherapy: a proof-of-concept study, Annals of Oncology, vol. 28, Issue 8, Apr. 29, 2017, pp. 1996-2001.

Cai et al., ROS1 fusions in Chinese patients with non-small-cell lung cancer, Annals of Oncology, vol. 24, No. 7, Jul. 2013, pp. 1822-1827.

Carter, Methods and strategies for analyzing copy No. variation using DNA microarrays, Nature Genetics, vol. 39, Jul. 2007, pp. S16-S21.

Chaudhuri et al., Early Detection of Molecular Residual Disease in Localized Lung Cancer by Circulating Tumor DnA Profiling, Cancer Discovery, Dec. 2017, pp. 1394-1404.

Chen et al., Circulating Tumor DNA Detection in Early-Stage Non-Small Cell Lung Cancer Patients by Targeted Sequencing, Scientific Reports, 6:31985, Aug. 24, 2016, pp. 1-8.

Cibulskis et al., Sensitive detection of somatic point mutations in impure and heterogeneous cancer samples, Nature Biotechnology, vol. 31, No. 3, Mar. 2013, pp. 213-221.

Couraud et al., Noninvasive Diagnosis of Actionable Mutations by Deep Sequencing of Circulating Free DNA in Lung Cancer from Never-Smokers: A Proof-of-Concept Study from BioCAST/IFCT-1002, Clinical Cancer Research, Sep. 1, 2014, pp. 4163-4625.

Crowley et al., Liquid biopsy: monitoring cancer-genetics in the blood, Nature Reviews, Clinical Oncology, 2013, pp. 1-13.

Dear et al., Happy mapping: linkage mapping using a physical analogue of meiosis, Nucleic Acids Research, 1993, vol. 21, No. 1, pp. 13-20.

Diaz, Jr. et al., Insights into therapeutic resistance from whole-genome analyses of circulating tumor DNA, Oncotarget, Oct. 2013, vol. 4, No. 10, pp. 1856-1857.

Diehl et al., Detection and quantification of mutations in the plasma of patients with colorectal tumors, PNAS, Nov. 8, 2005, vol. 102, No. 45, pp. 16368-16373.

Dienstmann et al., Standardized decision support in next generation sequencing reports of somatic cancer variants, Molecular Oncology 8, 2014, pp. 859-873.

Ding et al., Somatic mutations affect key pathways in lung adenocarcinoma, Nature 455, No. 7216, Oct. 23, 2008, pp. 1069-1075.

Dong et al., Potential Predictive Value of TP53 and KRAS Mutation Status for Response to PD-1 Blockade Immunotherapy in Lung Adenocarcinoma, Clinical Cancer Research, 23(12), Jun. 15, 2017, pp. 3012-3025.

Duployez et al., Minimal residual disease monitoring in t(8;21) acute myeloid leukemia based on RUNX1-RUNX1T1 fusion quantification on genomic DNA, American Journal of Hematology, vol. 89, No. 6, Jun. 2014, pp. 610-615.

Durendez Saez et al., New insights in non-small-cell lung cancer: circulating tumor cells and cell-free DNA, Journal of Thoracic Disease, vol. 9, Suppl. 13, Oct. 13, 2017, pp. S1332-S1345.

(56) References Cited

OTHER PUBLICATIONS

Ettinger et al., Non-Small Cell Lung Cancer, Version 5.2017, Journal of the National Comprehensive Cancer Network, vol. 15, No. 4, Apr. 2017, pp. 504-535.

Fernandez-Cuesta et al., Identification of Circulating Tumor DNA for the Early Detection of Small-cell Lung Cancer, EBioMedicine 10, Jun. 25, 2016, pp. 117-123.

Frenel et al., Serial Next-Generation Sequencing of Circulating Cell-Free DNA Evaluating Tumor Clone Response to Molecularly Targeted Drug Administration, Clinical Cancer Resesarch, 21(20), Oct. 15, 2015, pp. 4586-4597.

Goetz et al., First-in-Human Phase I Study of the Tamoxifen Metabolite Z-Endoxifen in Women With Endocrine-Refractory Metastatic Breast Cancer, Journal of Clinical Oncology, vol. 35, No. 30, Oct. 20, 2017, pp. 3391-3406.

Haigis, KRAS Alleles: The Devil Is in the Detail, Trends in Cancer, 3(10), Oct. 2017, pp. 1-20.

Hainaut et al., Patterns of p53 G-T transversions in lung cancers reflect the primary mutagenic signature of DNA-damage by tobacco smoke, Carcinogenesis, vol. 22, No. 3, 2001, pp. 367-374.

Hardwick et al., Reference standards for next-generation sequencing, Nature Reviews, Genetics, vol. 18, Aug. 2017, pp. 473-484.

Haselmann et al., Liquid Profiling of Circulating Tumor DNA in Plasma of Melanoma Patients for Companion Diagnostics and Monitoring of BRAF Inhibitor Therapy, Clinical Chemistry, 64:5, 2018, pp. 830-842.

Hoffmann et al., DNA bar coding and pyrosequencing to identify rare HIV drug resistance mutations, Nucleic Acids Research, vol. 35, No. 13, e91, Jun. 18, 2007, pp. 1-8.

Huang et al., Radiographic changes after lung stereotactic ablative radiotherapy (SABR)—Can we distinguish recurrence from fibrosis? A systematic review of the literature, Radiotherapy and Oncology, 102, Feb. 1, 2012, pp. 335-342.

Jamal-Hanjani et al., Detection of ubiquitous and heterogeneous mutations in cell-free DNA from patients with early-stage non-small-cell lung cancer, Annals of Oncology, vol. 27, No. 5, May 2016, pp. 862-867.

Jenkins et al., Plasma ctDNA Analysis for Detection of the EGFR T790M Mutation in Patients with Advanced Non-Small Cell Lung Cancer, Journal of Thoracic Oncology, vol. 12, No. 7, Apr. 17, 2017, pp. 1061-1070.

Khoo et al., Molecular methods for somatic mutation testing in lung adenocarcinoma: EGFR and beyond, Transitional Lung Cancer Research, vol. 4, No. 2, Apr. 2015, pp. 126-141.

Kinde et al., FAST-SeqS: A Simple and Efficient Method for the Detection of Aneuploidy by Massively Parallel Sequencing, PLOS One, vol. 7, Issue 7, e41162, Jul. 2012, pp. 1-8.

Kirkizlar et al., Detection of Clonal and Subclonal Copy-Number Variants in Cell-Free DNA from Patients with Breast Cancer Using a Massively Multiplexed PCR Methodology, Translational Oncology, vol. 8, No. 5, Oct. 2015, pp. 407-416.

Kocak et al., Challenges in Defining Radiation Pneumonitis in Patients With Lung Cancer, Int. J. Radiation Oncology, Biology, Physics, vol. 62, No. 3, 2005, pp. 635-638.

Kohno et al., Beyond ALK-RET, ROS1 and other oncogene fusions in lung cancer, Transational Lung Cancer Research, vol. 4, No. 2, Apr. 2015, pp. 156-164.

Lanman et al., Analytical and Clinical Validation of a Digital Sequencing Panel for Quantitative, Highly Accurate Evaluation of Cell-Free Circulating Tumor DNA, PLOS One, Oct. 16, 2015, pp. 1-27.

Le Calvez et al., TP53 and KRAS Mutation Load and Types in Lung Cancers in Relation to Tobacco Smoke: Distinct Patterns in Never, Former, and Current Smokers, Cancer Research, 65: (12), Jun. 15, 2005, pp. 5076-5084.

Leary et al., Development of Personalized Tumor Biomarkers Using Massively Parallel Sequencing, Sci Transl Med, 2(20), Feb. 24, 2010, pp. 1-15.

Levin et al., Targeted next-generation sequencing of a cancer transcriptome enhances detection of sequence variants and novel fusion transcripts, Genome, Biology 2009, vol. 10, Issue 10, Article R115, Oct. 16, 2009, pp. 1-8.

Lin et al., Δ-PCR, A Simple Method to Detect Translocations and Insertion/Deletion Mutations, The Journal of Molecular Diagnostics, vol. 13, No. 1, Jan. 2011, pp. 85-92.

Maher et al., Chimeric transcript discovery by paired-end transcriptome sequencing, PNAS, vol. 106, No. 30, Jul. 28, 2009, pp. 12353-12358.

McCaughan et al., Single-molecule genomics, Journal of Pathology, 220, Nov. 19, 2009, pp. 297-306.

Metz et al., Ultradeep sequencing detects GNAQ and GNA11 mutations in cell-free DNA from plasma of patients with uveal melanoma, Cancer Medicine, 2(2), 2013, pp. 208-215.

Metzler et al., Asymmetric multiplex-polymerase chain reaction—a high throughput method for detection and sequencing genomic fusion sites in t(4;11), British Journal of Haematology, 124, 2004, pp. 47-54.

|     | R1  | R2  | R3  | R4  |     |
| --- | --- | --- | --- | --- | --- |
|     | —   | —   | —   | —   | A1  |
|     | —   | —   | —   |     | A2  |
|     | —   | —   | —   | —   | A3  |
|     |     | —   |     | —   | A4  |
|     | —   | —   | —   | —   | A5  |
|     | —   | —   | —   |     | A6  |
|     | —   | —   | —   | —   | A7  |
|     |     | —   | —   |     | A8  |

FIG. 1

METHOD FOR THE ANALYSIS OF MINIMAL RESIDUAL DISEASE

CROSS-REFERENCING

This application is a continuation of U.S. application Ser. No. 18/123,235, filed on Mar. 17, 2023, which is a continuation of U.S. application Ser. No. 18/088,402, filed on Dec. 23, 2022, which is a continuation of U.S. application Ser. No. 16/749,858, filed on Jan. 22, 2020, now issued as U.S. Pat. No. 11,566,274, which is a continuation of International Application No. PCT/IB2019/056625, filed on Aug. 2, 2019, which claims the benefit of U.S. provisional application Ser. No. 62/716,082, filed on Aug. 8, 2018, which applications are incorporated by reference herein.

BACKGROUND

Many diseases are caused by genetic variations, e.g., somatic mutations. Because genetic variations often only occur in a fraction of the cells in the body, they can be challenging to detect by next generation sequencing (NGS). One problem is that every library preparation method and sequencing platform results in sequence reads that contain errors, e.g., PCR errors and sequencing errors. While it is sometimes possible to correct systematic errors (e.g., those that are correlated with known parameters including sequencing cycle-number, strand, sequence-context and base substitution probabilities), it is often impossible to figure out with any certainty whether a variation in a sequence is caused by an error or if it is a "real" genetic variation. This problem is exacerbated if the amount of sample is limited and mutation-containing polynucleotides are present only at relatively low levels, e.g., less than 5%, in the sample as is typically the case for cell-free DNA isolated from blood. For example, if a sample contains only one copy of a mutation-containing polynucleotide in a background of a hundred polynucleotides that are otherwise identical to the mutation-containing polynucleotide except that they do not contain the mutation, then, after those polynucleotides have been sequenced, it can often be impossible to tell whether the variation (which may only be observed in about 1/100 of the sequence reads) is an error that occurred during amplification or sequencing. Thus, the detection of somatic mutations that cause diseases can be extremely difficult to detect with any certainty.

SUMMARY

Described below is a workflow that facilitates identification of low frequency sequence variations, e.g., cell-free DNA from blood. In some embodiments, the method may comprise analyzing PCR reactions that each contain different portions of the same sample, wherein at least some of the primer pairs are in more than one PCR reaction and at least one of the PCR reactions contains some but not all of the primer pairs of the other reaction(s). In this method, some primer pairs are in more of the reactions than others, depending upon a number of factors.

In some embodiments, the method may comprise:
  (a) obtaining multiple pairs of primers that are compatible in a multiplex PCR reaction;
  (b) setting up at least two multiplex PCR reactions each containing different portions of the same sample, wherein at least some of the primer pairs are in more than one PCR reaction and at least one of the PCR reactions contains some but not all of the primer pairs of the other reaction(s), wherein, for at least some of the primer pairs that are not in all PCR reactions, the number of reactions comprising a primer pair depends on the perceived importance of, the likelihood of and/or the type of one or more sequence variations expected in the amplicon amplified by the primer pair;
  (c) thermocycling the multiplex PCR reactions to produce multiple replicate amplicons;
  (d) sequencing the amplicons to produce sequence reads;
  (e) analyzing the sequence reads from replicate amplicons for a selected sequence variation to produce a score for the selected sequence variation, wherein the score: i. is based on the number of replicate amplicons that comprise a sequence variation that has a frequency above a cut-off; or ii. indicates the strength of the combined evidence for the sequence variation across the replicates; and
  (f) calling a sequence variation based on the score.

Depending on how the method is implemented, the method may have certain advantages over the conventional methods. For example, the present method can provide a higher probability of identifying genetic variations deemed more important by the users of the method, without simply increasing the number of multiplex PCR reactions.

BRIEF DESCRIPTION OF THE FIGURES

The skilled artisan will understand that the drawings, described below, are for illustration purposes only. The drawings are not intended to limit the scope of the present teachings in any way.

FIG. 1 schematically illustrates an example of a set of multiplex PCR reactions that can be produced in the claimed method. This example simply illustrates some of the principles of the method and should not limit the method in any way.

DEFINITIONS

Figure 2:
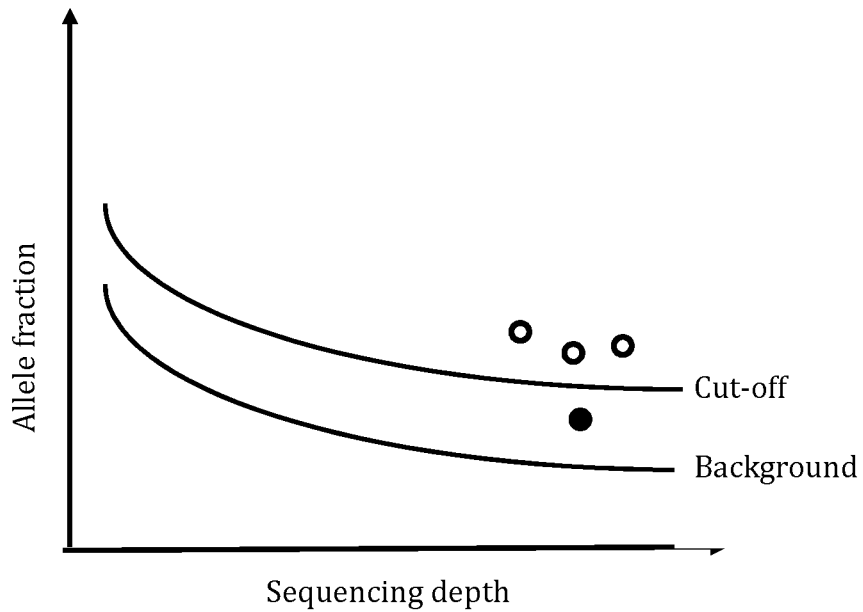
FIG. 2 illustrates how a genetic variation can be called using the number of replicates that have the selected sequence variation above a cutoff frequency.
Figure 3:
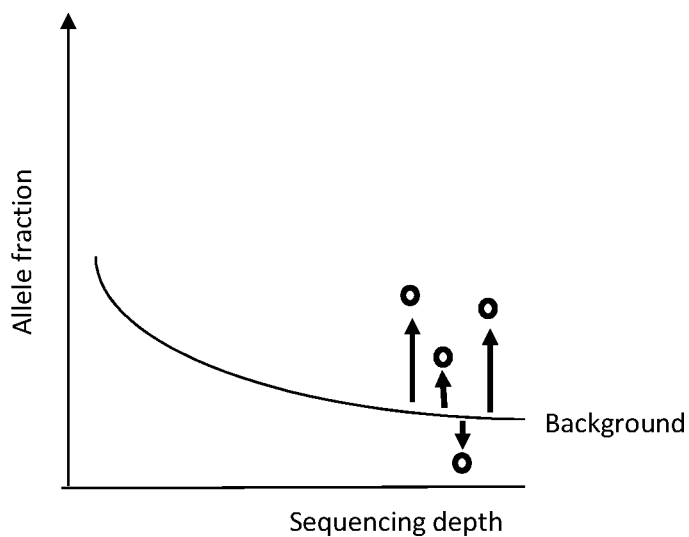
FIG. 3 illustrates how a genetic variation can be called by using the combined evidence for the genetic variation across multiple replicates.

Unless otherwise defined, all technical and scientific terms used herein have the same meaning as commonly understood by one of ordinary skill in the art to which this invention belongs. Still, certain elements are defined for the sake of clarity and ease of reference.

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, greater than 10,000 bases, greater than 100,000 bases, greater than about 1,000,000, up to about $10^{10}$ or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylenecarbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid," or "UNA," is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "nucleic acid sample," as used herein, denotes a sample containing nucleic acids. Nucleic acid samples used herein may be complex in that they contain multiple different molecules that contain sequences. Genomic DNA samples from a mammal (e.g., mouse or human) are types of complex samples. Complex samples may have more than about $10^4$, $10^5$, $10^6$ or $10^7$, $10^8$, $10^9$ or $10^{10}$ different nucleic acid molecules. Any sample containing nucleic acid, e.g., genomic DNA from tissue culture cells or a sample of tissue, may be employed herein.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers, or both ribonucleotide monomers and deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers are extended by a DNA polymerase. Primers are generally of a length compatible with their use in synthesis of primer extension products, and are usually in the range of 8 to 200 nucleotides in length, such as 10 to 100 or 15 to 80 nucleotides in length. A primer may contain a 5' tail that does not hybridize to the template.

Primers are usually single-stranded for maximum efficiency in amplification, but may alternatively be double-stranded or partially double-stranded. Also included in this definition are toehold exchange primers, as described in Zhang et al (Nature Chemistry 2012 4: 208-214), which is incorporated by reference herein.

Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The term "hybridization" or "hybridizes" refers to a process in which a region of nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strand region in a hybridization reaction. The hybridization reaction can be made to be highly specific by adjustment of the hybridization conditions under which the hybridization reaction takes place, such that two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.).

The term "duplex," or "duplexed," as used herein, describes two complementary polynucleotide region that are base-paired, i.e., hybridized together.

"Genetic locus," "locus,", "locus of interest", "region" or "segment" in reference to a genome or target polynucleotide, means a contiguous sub-region or segment of the genome or target polynucleotide. As used herein, genetic locus, locus, or locus of interest may refer to the position of a nucleotide, a gene or a portion of a gene in a genome or it may refer to any contiguous portion of genomic sequence whether or not it is within, or associated with, a gene, e.g., a coding sequence. A genetic locus, locus, or locus of interest can be from a single nucleotide to a segment of a few hundred or a few thousand nucleotides in length or more. In general, a locus of interest will have a reference sequence associated with it (see description of "reference sequence" below).

The term "reference sequence", as used herein, refers to a known nucleotide sequence, e.g. a chromosomal region whose sequence is deposited at NCBI's Genbank database or other databases, for example. A reference sequence can be a wild type sequence.

The terms "plurality", "population" and "collection" are used interchangeably to refer to something that contains at least 2 members. In certain cases, a plurality, population or collection may have at least 10, at least 100, at least 1,000, at least 10,000, at least 100,000, at least $10^6$, at least $10^7$, at least $10^8$ or at least $10^9$ or more members.

The term "sample identifier sequence", "sample index", "multiplex identifier" or "MID" is a sequence of nucleotides that is appended to a target polynucleotide, where the sequence identifies the source of the target polynucleotide (i.e., the sample from which sample the target polynucleotide is derived). In use, each sample is tagged with a different sample identifier sequence (e.g., one sequence is appended to each sample, where the different samples are appended to different sequences), and the tagged samples are pooled. After the pooled sample is sequenced, the sample identifier sequence can be used to identify the source of the sequences. A sample identifier sequence may be added to the 5' end of a polynucleotide or the 3' end of a polynucleotide. In certain cases some of the sample identifier sequence may be at the 5' end of a polynucleotide and the remainder of the sample identifier sequence may be at the 3' end of the polynucleotide. When elements of the sample identifier has sequence at each end, together, the 3' and 5' sample identifier sequences identify the sample. In many examples, the sample identifier sequence is only a subset of the bases which are appended to a target oligonucleotide.

The term "replicate identifier sequence" refers to an appended sequence that allows sequence reads from different replicates to be distinguished from one another. Replicate identifier sequences work in the same way as sample identifier sequences described above, except that they are used on replicates of a sample, rather than different samples.

The term "variable", in the context of two or more nucleic acid sequences that are variable, refers to two or more nucleic acids that have different sequences of nucleotides relative to one another. In other words, if the polynucleotides of a population have a variable sequence, then the nucleotide sequence of the polynucleotide molecules of the population may vary from molecule to molecule. The term "variable" is not to be read to require that every molecule in a population has a different sequence to the other molecules in a population.

The term "substantially" refers to sequences that are near-duplicates as measured by a similarity function, including but not limited to a Hamming distance, Levenshtein distance, Jaccard distance, cosine distance etc. (see, generally, Kemena et al, Bioinformatics 2009 25: 2455-65). The exact threshold depends on the error rate of the sample preparation and sequencing used to perform the analysis, with higher error rates requiring lower thresholds of similarity. In certain cases, substantially identical sequences have at least 98% or at least 99% sequence identity.

The term "sequence variation", as used herein, is a variant that is present a frequency of less than 50%, relative to other molecules in the sample, where the other molecules in the sample are substantially identical to the molecules that contain the sequence variation. In some cases, a particular sequence variation may be present in a sample at a frequency of less than 20%, less than 10%, less than 5%, less than 1% or less than 0.5%.

The term "nucleic acid template" is intended to refer to the initial nucleic acid molecule that is copied during amplification. Copying in this context can include the formation of the complement of a particular single-stranded nucleic acid. The "initial" nucleic acid can comprise nucleic acids that have already been processed, e.g., amplified, extended, labeled with adaptors, etc.

The term "tailed", in the context of a tailed primer or a primer that has a 5' tail, refers to a primer that has a region (e.g., a region of at least 12-50 nucleotides) at its 5' end that does not hybridize or partially hybridizes to the same target as the 3' end of the primer.

The term "initial template" refers to a sample that contains a target sequence to be amplified. The term "amplifying" as used herein refers to generating one or more copies of a target nucleic acid, using the target nucleic acid as a template.

The term "amplicon" as used herein refers to the product (or "band") amplified by a particular pair of primers in a PCR reaction.

The "replicate amplicon" as used herein refers to the same amplicon amplified using different portions of a sample. Replicate amplicons typical have near identical sequences, except for sequence variations in the template, PCR errors, and differences in the sequences of the primers used for each replicate (e.g., differences in the 5' ends of the primers such as in the replicate identifier sequence, etc.).

A "polymerase chain reaction" or "PCR" is an enzymatic reaction in which a specific template DNA is amplified using one or more pairs of sequence specific primers.

"PCR conditions" are the conditions in which PCR is performed, and include the presence of reagents (e.g., nucleotides, buffer, polymerase, etc.) as well as temperature cycling (e.g., through cycles of temperatures suitable for denaturation, renaturation and extension), as is known in the art.

A "multiplex polymerase chain reaction" or "multiplex PCR" is an enzymatic reaction that employs two or more primer pairs for different targets templates. If the target templates are present in the reaction, a multiplex polymerase chain reaction results in two or more amplified DNA products that are co-amplified in a single reaction using a corresponding number of sequence-specific primer pairs.

The term "sequence-specific primer" as used herein refers to a primer that only binds to and extends at a unique site in a sample under study. In certain embodiments, a "sequence-specific" oligonucleotide may hybridize to a complementary nucleotide sequence that is unique in a sample under study.

The term "next generation sequencing" refers to the so-called highly parallelized methods of performing nucleic acid sequencing and comprises the sequencing-by-synthesis or sequencing-by-ligation platforms currently employed by Illumina, Life Technologies, Pacific Biosciences and Roche, etc. Next generation sequencing methods may also include, but not be limited to, nanopore sequencing methods such as offered by Oxford Nanopore or electronic detection-based methods such as the Ion Torrent technology commercialized by Life Technologies.

The term "sequence read" refers to the output of a sequencer. A sequence read typically contains a string of Gs, As, Ts and Cs, of 50-1000 or more bases in length and, in many cases, each base of a sequence read may be associated with a score indicating the quality of the base call.

The terms "assessing the presence of" and "evaluating the presence of" include any form of measurement, including determining if an element is present and estimating the amount of the element. The terms "determining", "measuring", "evaluating", "assessing" and "assaying" are used interchangeably and include quantitative and qualitative determinations. Assessing may be relative or absolute. "Assessing the presence of" includes determining the amount of something present, and/or determining whether it is present or absent.

If two nucleic acids are "complementary," they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

An "oligonucleotide binding site" refers to a site to which an oligonucleotide hybridizes in a target polynucleotide. If an oligonucleotide "provides" a binding site for a primer, then the primer may hybridize to that oligonucleotide or its complement.

The term "strand" as used herein refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "extending", as used herein, refers to the extension of a primer by the addition of nucleotides using a polymerase. If a primer that is annealed to a nucleic acid is extended, the nucleic acid acts as a template for extension reaction.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

The term "pooling", as used herein, refers to the combining, e.g., mixing, of two or more samples or replicates of a sample such that the molecules within those samples or replicates become interspersed with one another in solution.

The term "pooled sample", as used herein, refers to the product of pooling.

The term "portion", as used herein in the context of different portions of the same sample, refers to an aliquot or part of a sample. For example, if one microliter of 100 ul sample is added to each of 10 different PCR reactions, then those reactions each contain different portions of the same sample.

As used herein, the terms "cell-free DNA from the bloodstream" "circulating cell-free DNA" and cell-free DNA" ("cfDNA") refers to DNA that is circulating in the peripheral blood of a patient. The DNA molecules in cell-free DNA may have a median size that is below 1 kb (e.g., in the range of 50 bp to 500 bp, 80 bp to 400 bp, or 100-1,000 bp), although fragments having a median size outside of this range may be present. Cell-free DNA may contain circulating tumor DNA (ctDNA), i.e., tumor DNA circulating freely in the blood of a cancer patient or circulating fetal DNA (if the subject is a pregnant female). cfDNA can be obtained by centrifuging whole blood to remove all cells, and then isolating the DNA from the remaining plasma or serum. Such methods are well known (see, e.g., Lo et al, Am J Hum Genet 1998; 62:768-75). Circulating cell-free DNA can be double-stranded or single-stranded. This term is intended to encompass free DNA molecules that are circulating in the bloodstream as well as DNA molecules that are present in extra-cellular vesicles (such as exosomes) that are circulating in the bloodstream.

As used herein, the term "circulating tumor DNA" (or "ctDNA") is tumor-derived DNA that is circulating in the peripheral blood of a patient. ctDNA is of tumor origin and originates directly from the tumor or from circulating tumor cells (CTCs), which are viable, intact tumor cells that shed from primary tumors and enter the bloodstream or lymphatic system. The precise mechanism of ctDNA release is unclear, although it is postulated to involve apoptosis and necrosis from dying cells, or active release from viable tumor cells. ctDNA can be highly fragmented and in some cases can have a mean fragment size about 100-250 bp, e.g., 150 to 200 bp long. The amount of ctDNA in a sample of circulating cell-free DNA isolated from a cancer patient varies greatly: typical samples contain less than 10% ctDNA, although many samples have less than 1% ctDNA and some samples have over 10% ctDNA. Molecules of ctDNA can be often identified because they contain tumorigenic mutations.

As used herein, the terms "cell-free RNA from the bloodstream" "circulating cell-free RNA" and cell-free RNA" ("cfRNA") refers to RNA that is circulating in the peripheral blood of a patient. Cell-free RNA may contain circulating tumor RNA (ctRNA), i.e., tumor RNA circulating freely in the blood of a cancer patient or circulating fetal RNA (if the subject is a pregnant female). This term is intended to encompass free RNA molecules that are circulating in the bloodstream as well as RNA molecules that are present in extra-cellular vesicles (such as exosomes) that are circulating in the bloodstream.

As used herein, the term "sequence variation" refers to the combination of a position and type of a sequence alteration. For example, a sequence variation can be referred to by the position of the variation and which type of substitution (e.g., G to A, G to T, G to C, A to G, etc. or insertion/deletion of a G, A, T or C, etc.) is present at the position. A sequence variation may be a substitution, deletion, insertion or rearrangement of one or more nucleotides. In the context of the present method, a sequence variation can be generated by, e.g., a PCR error, an error in sequencing or a genetic variation.

As used herein, the term "genetic variation" refers to a variation (e.g., a nucleotide substitution, an indel or a rearrangement) that is present or deemed as being likely to be present in a nucleic acid sample. A genetic variation can be from any source. For example, a genetic variation can be generated by a mutation (e.g., a somatic mutation), an organ transplant or pregnancy. If sequence variation is called as a genetic variation, the call indicates that the sample likely contains the variation; in some cases a "call" can be incorrect. In many cases, the term "genetic variation" can be replaced by the term "mutation". For example, if the method is being uses to detect sequence variations that are associated with cancer or other diseases that are caused by mutations, then "genetic variation" can be replaced by the term "mutation".

As used herein, the term "calling" means indicating whether a particular sequence variation is present in a sample. This may involve, for example, providing a sequence that contains the sequence variation and/or annotating a sequence having the sequence variation, indicating that the sequence has an A to T variation at a specific position.

As used herein, the term "threshold" refers to a level of evidence that is required to make a call. A threshold i. can vary from one sequence variation to another and ii. in some cases may be increased or decreased independently of other thresholds, as desired, depending on a variety of factors.

As used herein, the term "cut-off" refers to a frequency of sequence reads at or above which a replicate can be identified as statistically likely to contain a sequence variation based on controls. As will be explained in greater detail below, in sequencing a PCR product that contains a sequence variation that is present in a minority of the molecules, some of the sequence reads will be from the variant molecules while others will not (e.g., will be from the "wild type" sequence). The frequency of reads that are from the variant molecules can be calculated by, for example, dividing the number of reads from the variant molecules by the total number of reads. The cut-off frequency can be established by sequencing several control samples (e.g., samples that do not contain the sequence variation). A cut-off i. can vary from one sequence variation to another and ii. in some cases may be increased or decreased independently of other cut-offs, as desired, depending on a variety of factors.

As used herein, the term "value" refers to a number, letter, word (e.g., "high", "medium" or "low") or descriptor (e.g., "+++" or "++") that can indicate the strength of evidence. A value can contain one component (e.g., a single number) or more than one component, depending on how a value is analyzed.

Other definitions of terms may appear throughout the specification. It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

DETAILED DESCRIPTION

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Provided herein is a method for sequence analysis that employs multiple pairs of primers that are compatible in a multiplex PCR reaction. In this context, a multiplex PCR reaction that contains "compatible" primers is one in which the pairs of primers are designed to specifically amplify regions of interest producing amplicons that correspond to the PCR primer pairs while minimizing the production of primer dimers, when the reaction is subjected to appropriate thermocycling conditions with an appropriate template for the primers. Typically, although not always, each primer pair amplifies a single region of interest in a multiplex PCR reaction. Conditions for performing multiplex PCR and programs for designing compatible primers are well known (see, e.g., Sint et al, Methods Ecol Evol. 2012 3: 898-90 and Shen et al BMC Bioinformatics 2010 11: 143). Compatible primer pairs may be designed using any one of a number of different programs specifically designed to design primer pairs for multiplex PCR methods. For example, the primer pairs may be designed using the methods of Yamada et al. (Nucleic Acids Res. 2006 34:W665-9), Lee et al. (Appl. Bioinformatics 2006 5:99-109), Vallone et al. (Biotechniques. 2004 37: 226-31), Rachlin et al. BMC Genomics. 2005 6:102 or Gorelenkov et al. (Biotechniques. 2001 31: 1326-30), for example. In some embodiments, the method may employ at least 5 pairs of compatible primers, e.g., at least 10, at least 50, at least 100 or at least 1,000 pairs of compatible primers. In some embodiments, the method may employ at least 10 and up to 50,000 primer pairs, at least 10 and up to 10,000 primer pairs, at least 10 and up to 5,000 primer pairs, at least 10 and up to 1,000 primer pairs or at least 10 and up to 500 primer pairs, where each primer pair is designed to amplify a different amplicon. The amplicons amplified can be of any suitable length and may vary in length. In some embodiments, the length of each amplicon, independently, may be in the range of 50 bp to 500 bp, although longer or shorter amplicons may be used in some implementations.

After the primer pairs have been obtained, the method may comprise setting up at least two multiplex PCR reactions (e.g., up to 10 multiplex PCR reactions, such as 2, 3, 4, 5, 6, 7, 8, 9 or 10 multiplex PCR reactions) each containing different portions of the same sample (i.e., different aliquots of the same sample). In this step, the multiplex PCR reactions are not identical to one another in that some primer pairs may be in all reactions whereas others are only in one or some (but not all) of the reactions. For example, if there are three multiplex PCR reactions, then some primer pairs may be in a single reaction, some primer pairs may be in two reactions, and some primer pairs may be in all three reactions. Likewise, if there are four multiplex PCR reactions, then some primer pairs may be in a single reaction, some primer pairs may be in two reactions, some primer pairs may be in three reactions and some primer pairs may be in all four reactions. In these embodiments, at least some of the primer pairs are in more than one PCR reaction and at least one of the PCR reactions contains some but not all of the primer pairs of the other reaction(s). How many PCR reactions contain a particular primer pair is determined by a variety of factors including, but not limited to: i. the likelihood of finding a genetic variation in the amplicon amplified by the selected primer pair, ii. the likelihood of finding a genetic variation that correlates with a particular cancer of interest in the amplicon amplified by the selected primer pair, iii. the treatment history of the patient from which the sample was obtained, iv. the likelihood of finding a clinically significant genetic variation in the amplicon amplified by the selected primer pair, v. previous tests undergone by the patient from which the sample was obtained, vi. the error profile of a genetic variation expected to be found in the amplicon amplified by the selected primer pair (where the term "error profile" indicates the frequency that a particular variation is not due to a genetic variation), and/or vii. the length of the amplicon amplified by the selected primer pair, or any combination thereof.

For example, if the likelihood of detecting a genetic variation in the amplicon amplified by a selected primer pair is high relative to the amplicons amplified by other primer pairs (as predicted by prior and ongoing experiments) then that primer pair may be in more reactions (e.g., all reactions). Conversely, if the likelihood of detecting a genetic variation in the amplicon amplified by a selected primer pair is low relative to the amplicons amplified by other primer pairs (as predicted by prior and ongoing experiments) then that primer pair may be in less reactions (e.g., one or two reactions). In another example, if the likelihood of finding a genetic variation that correlates with a particular disease or conditions (e.g., a cancer of interest) is high in one amplicon compared to other amplicons, then the primer pair may be in more reactions (e.g., all reactions). For example, if one is more interested in testing for mutations that are associated with non-small cell lung cancer, then the primer pairs that amplify sequences that potentially contain those mutations may be in more reactions. Conversely, primers pairs that amplify fragments that potentially contain genetic variations that correlate with diseases or conditions that are of no interest to the researcher may be in less reactions (e.g., one or two reactions). In another example, the treatment history of the patient from which the sample was obtained may be used to determine how many reactions contain a particular primer pair. In this example, primer pairs that amplify sequences that can harbor genetic variations that are associated with resistance to the treatment can be in more reactions (e.g., all reactions), whereas primer pairs that amplify sequences that can harbor genetic variations that are not associated with resistance to the treatment can be in less reactions, e.g., one or two reactions. In another example, primer pairs that amplify sequences that may harbor clinically actionable genetic variations (i.e., genetic variations that correlate with a successful treatment) may be in more reactions (e.g. all reactions), whereas primer pairs that amplify sequences that do not harbor clinically actionable genetic variations may be in less reactions (e.g., one or two reactions). In another example, the number of reactions that contain a particular primer pair may be determined by previous tests undergone by the patient from which the sample was obtained. For example, if the patient is already known to have a particular genetic variation, a primer pair that amplifies an amplicon that potentially contains that genetic variation may be in more (e.g., all) reactions and a primer pair that does not amplify an amplicon that potentially contains the genetic variation may be in less (e.g., one or two) reactions. In another example the number of reactions that contain a particular primer pair may be determined by the type of genetic variation found in the amplicon amplified by the primer pair. Certain types of sequence variations (e.g., indels and rearrangements) are unlikely to have been be generated by a PCR and/or sequencing error and, as such, primer pairs that target indels can be in less reactions (e.g., one or two reactions). Primer pairs that target variations that have a higher background (e.g., nucleotide substitutions) can be in more reactions (e.g., all reactions). In another example, primer pairs that amplify longer products may be in more reactions than primer pairs that amplify shorter products because, when the DNA of interest is fragmented as is the case for cell free DNA, the primer pairs that amplify longer products will more frequently fail to amplify the available DNA than will the primer pairs that amplify shorter products.

Figure 1:
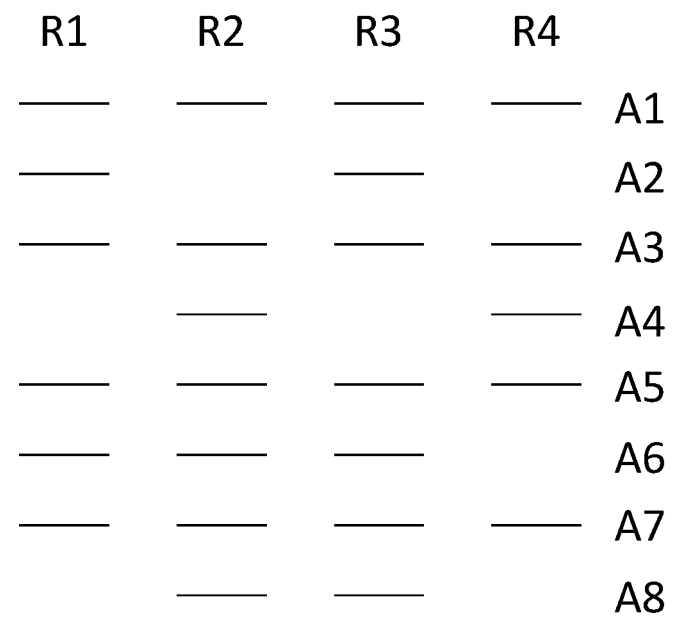

A schematic illustration of four multiplex PCR reactions (R1, R2, R3 and R4) that have been set up according to the principle described above is shown in FIG. 1. In this example, amplicon A1 has a high likelihood of containing a genetic variation relative to other amplicons and, as such, the pair of PCR primers that produces this amplicon is in all reactions; amplicon A2 has a low likelihood of containing a genetic variation relative to other amplicons and, as such, the pair of PCR primers that produces this amplicon is in two reactions; amplicon A3 has a higher likelihood of containing a genetic variation that is associated with a particular cancer of interest, e.g., non-small cell lung cancer, relative to other amplicons and, as such, the pair of PCR primers that produces this amplicon is in all reactions; amplicon A4 has a lower likelihood of containing a genetic variation that is associated with a particular cancer of interest relative to other amplicons and, as such, the pair of PCR primers that produces this amplicon is in two amplicons; amplicon A5 has a higher likelihood of containing a clinically actionable genetic variation and, as such, the pair of PCR primers that produces this amplicon is in all reactions; amplicon A6 has a lower likelihood of containing a clinically actionable genetic variation and, as such, the pair of PCR primers that produces this amplicon is in only three reactions; amplicon A7 has a higher likelihood of containing a high background genetic variation and, as such, the pair of PCR primers that produces this amplicon is in all reactions; and amplicon A8 has a higher likelihood of containing a low background genetic variation (e.g., an indel or a translocation) and, as such, the pair of PCR primers that produces this amplicon is in two reactions. In some embodiments, the pairs of PCR primers that are in less reactions may be spread among the reactions so that each of the multiplex PCR reactions contains approximately the same number of primer pairs.

In some embodiments, the pairs of PCR primers that produce amplicons that have a higher likelihood of containing a genetic variation may be in more reactions than pairs of PCR primers that produce amplicons that have a lower likelihood of containing a genetic variation; pairs of PCR primers that produce amplicons that have a higher likelihood of containing a genetic variation that is associated with a particular cancer of interest may be in more reactions than pairs of PCR primers that produce amplicons that have a lower likelihood of containing a genetic variation that is associated with the particular cancer of interest; pairs of PCR primers that produce amplicons that have a higher likelihood of containing a genetic variation that makes a patient resistant to a therapy may be in more reactions than pairs of PCR primers that produce amplicons that have a lower likelihood of containing a genetic variation that make a patient resistant to the therapy; pairs of PCR primers that produce amplicons that have a higher likelihood of containing clinically actionable genetic variations may be in more reactions than pairs of PCR primers that produce amplicons that have a lower likelihood of containing clinically actionable genetic variations; and/or pairs of PCR primers that produce amplicons that have a higher likelihood of containing a high background genetic variation may be in more reactions than pairs of PCR primers that produce amplicons that have a higher likelihood of containing a low background genetic variation.

After the reactions have been set up, the method comprises placing the multiplex PCR reactions under suitable conditions for amplification (e.g., thermocycling) to produce multiple replicate amplicons, where "replicate" amplicons are amplicons that are amplified by the same primers in two or more reactions. Replicate amplicons generally have the same sequence (except for PCR errors, variations corresponding to genetic variations in the sample and any variations in the PCR primers). Illustrated by example, all of the amplicons shown in FIG. 1 have replicates: amplicon A1 has four replicates, amplicon A2 has two replicates and amplicon A3 has four replicates, etc. The amplicons are then sequenced to produce sequence reads.

In sequencing the amplicons, the amplicons derived from each different multiplex PCR reaction may be sequenced separately to one another or the amplicons may be barcoded with a replicate identifier and then pooled prior to sequencing. In some embodiments, the primers in the multiplex PCR reactions may have a 5' tail that contains the replicate identifier such that, after the PCR reactions have been completed, the sequence of the 5' tail of the primers is present in the amplicons. In other embodiments, the multiplex PCR reactions can be done without using primers that have a 5' tail that contains a replicate identifier. In these embodiments, the PCR products may be barcoded with a replicate identifier in a second round of amplification that uses PCR primers that have a 5' tail containing a replicate identifier. Either way, the amplicons may be amplified prior to sequencing, using primers that have a 5' tail that provides compatibility with a particular sequencing platform. In certain embodiments, in addition to a replicate identifier, one or more of the primers used in this step may additionally contain a sample identifier. If the primers have a sample identifier, then products derived from different samples can be pooled prior to sequencing. In some embodiments, the target specific primers contain from 5' to 3' a universal "tagging" sequence, an optional replicate barcode sequence followed by a sequence designed to the target of interest. The primers used to further amplify the initial multiplex contain from 5' to 3' a tail that provides compatibility with a particular sequencing platform, a sample barcode and optionally a replicate barcode, and a sequence that can bind to either part or all of the reverse complement of the tagging sequence present on the target specific primers. Typically, the forward and reverse primers will have different tagging sequences.

The primers used for the amplification step may be compatible with use in any next generation sequencing platform in which primer extension is used, e.g., Illumina's reversible terminator method, Roche's pyrosequencing method (454), Life Technologies' sequencing by ligation (the SOLiD platform), Life Technologies' Ion Torrent platform or Pacific Biosciences' fluorescent base-cleavage method. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) English (PLoS One. 2012 7: e47768) and Morozova (Genomics. 2008 92:255-64), which are incorporated by reference for the general descriptions of the methods and the particular steps of the methods, including all starting products, reagents, and final products for each of the steps.

The sequencing step may be done using any convenient next generation sequencing method and may result in at least 10,000, at least 50,000, at least 100,000, at least 500,000, at least 1M at least 10M at least 100M, at least 1B or at least 10B sequence reads. In some cases, the reads may be paired-end reads.

The sequence reads are then processed computationally. The initial processing steps may include identification of barcodes (including sample identifiers or replicate identifier sequences), and trimming reads to remove low quality or adaptor sequences. In addition, quality assessment metrics can be run to ensure that the dataset is of an acceptable quality.

After the sequence reads have undergone initial processing, they are analyzed to identify genetic variations. Calling genetic variations in cell-free DNA can be challenging because the variant sequences are generally in the minority (e.g., less than 10% of the sequence). As such, if an amplicon sequencing strategy is employed, the sequences for each amplicon may be mostly wild type sequences. Minority variants, which may be represented by less than 10% of the sequences, are difficult to distinguish from artefacts, e.g., sequencing and/or PCR errors. In the present method, the amplicons are analyzed to produce a score that, for each sequence variation, indicates whether the sequence variation is likely to represent a genetic variation (e.g., a mutation in the DNA in the sample), as opposed to a PCR error or sequencing artifact. In these embodiments, the method may comprise analyzing the sequence reads from replicate amplicons for a selected sequence variation to produce a score for the selected sequence variation. In these embodiments, the score may be based on the number of replicate amplicons that comprise a sequence variation that has a frequency above a cut-off or may indicate the strength of the combined evidence for the sequence variation across the replicates. A sequence variation may be called as a genetic variation based on the score. In some embodiments, the genetic variation may be called comparing the score to a threshold. The genetic variation can be called if the score is at or above the threshold.

In embodiments in which the score is based on the number of replicate amplicons that comprise a sequence variation that has a frequency above a cut-off, the cut-off may be based on an error distribution that indicates how often a sequence variation is generated by an amplification and/or sequencing error. This error distribution may be established using control samples that may or may not have genetic variations. In some embodiments a cut-off may be determined using a binomial, overdispersed binomial, beta, normal, exponential or gamma probability distribution model based on the sequencing of control samples. In some embodiments, an error distribution may show how often amplification and/or sequencing errors occur at different sequencing depths. An example of such an error distribution is shown in FIG. 2. In the example shown in FIG. 2, the frequency of a sequence variation at each position in an amplicon (i.e., the number of sequence reads that contain a sequence variation at a position relative to the total number of sequence reads for that position) can be plotted against sequencing depth (i.e., total number of sequence reads) for a number of control samples in order to establish the background level of sequence variation for each position (which background is presumably due to sequencing artefacts, rather than a genetic variation). In this example, the "cut-off" establishes a baseline for identifying variations that are statistically unlikely to be background. In these embodiments, the number of replicate amplicons that comprise a sequence variation that has a frequency that is above a cut-off provides a score that can be used to determine whether a variation is a genetic variation. For example, in the example shown in FIG. 2, the frequency of the variant is above the cutoff in three of the four replicates. In this example, the score could be "3 out of 4", 0.75, or simply "3", indicating that the variation has been positively identified in three replicates. This score is then compared to a threshold in order to determine whether the variation is likely to be the result of a genetic variation. This threshold can vary from position to position and need not be the same for every potential genetic variation. For example, in the example shown in FIG. 2, the threshold could be, for example, 2 or 3, in which case the variant whose data is shown in FIG. 2 is likely be due to a genetic variation because the number of replicates in which the variation is found is at or above the cut-off. If the threshold is 4 in this example, then the variation may not be called as a genetic variation because the score is below the threshold. As would be appreciated, a threshold may be increased or decreased depending on how many replicates of an amplicon are sequenced and a number of other factors. The cut-off may also be increased or decreased based on a number of factors. In some embodiments, this method may comprise (i) for each nucleotide position of a particular amplicon, determining, e.g., plotting, an error distribution that shows how often amplification and/or sequencing errors occur at different sequencing depths; (ii) based on the distribution for each position of the sequence, determining a cut-off for each different sequencing depth at or above which a genetic variation can be detected; (iii) sequencing multiple replicate amplicons from the same sample to obtain a plurality of reads for the replicate amplicons; and (iv) determining, for each position of an amplicon, whether the frequency of a sequence variation in the sequence reads is above or below the cut-off. The number of amplicons at or above the cut-off provides the score. In these embodiments, the term "plotting" may be done computationally and, as such, the method can be done without physically drawing a graph.

In embodiments in which the score indicates the strength of the combined evidence for the sequence variation across the replicates, the data may be subjected to statistical procedures, either frequentist or Bayesian and the evidence for the variation may be summarized as a likelihood value, or alternatively a Bayes factor or a posterior probability in the context of a Bayesian analysis. In these embodiments, this statistical score can be altered by other data as it accumulates. For example, the combined evidence for a sequence variation (which evidence may include, for example, the number of replicates in which sequence reads having the variation have been identified and, for each amplicon: i. the number of sequence reads having the variation, ii. the total number of sequence reads for the amplicon, iii. the frequency of the genetic variation in the sequence reads and, iv other metrics) can be summarized as a score (e.g., a P-value or the like), and the score can be compared to a threshold to determine if the variation can be called as a genetic variation. For example, if the score summarizing the combined evidence is 0.91 and the likelihood threshold for calling a genetic variation is 0.95, then the genetic variation may not be called. On the other hand, if the score summarizing the combined evidence is 0.98 and the likelihood threshold for calling a genetic variation is 0.95, then the genetic variation should be called. These analysis methods as well as the threshold can be done by machine learning, if desired.

However the sequence analysis step is implemented, the threshold or cut-off used can, itself, be increased or decreased for each variation as data accumulates and/or other factors. For example, the threshold and/or cut-off itself can be increased or decreased using similar factors to those described above. For example, the threshold and/or cut-off can be increased or decreased based on the expected frequency of a particular genetic variation in cancer patients (in which case the threshold and/or cut-off may be lower for more common mutations), the type of cancer of the patient from which the sample was obtained (in which case the threshold and/or cut-off may be lower for mutations associated with a cancer of interest such as non-small cell lung cancer), the treatment history of the patient from which the sample was obtained (in which case the threshold and/or cut-off may be lower for genetic variations associated with resistance to a treatment), the clinical significance of genetic variations (in which case the threshold and/or cut-off may be lower for genetic variations associated with a treatment for a cancer), previous tests undergone by the patient (in which case the threshold and/or cut-off may be lower for genetic variations that have already been identified in the patient), the error profile of a variation (in which case the threshold and/or cut-off may be lower for genetic variations with lower error rate), other genetic variations that are found in the sample (in which case the threshold and/or cut-off may be lower for genetic variations that are not commonly found together in a sample) and/or the overall error rate of the sequencing.

In some embodiments, the sample may be cfDNA and the method may further comprise sequencing at least some of the same regions amplified using cfRNA from the same subject (via RT-PCR). This may be performed either using the same amplicons or different amplicons. In this implementation, the method may involve comparing the genetic variations called using cfDNA to the genetic variations called using cfRNA. If a variation is identified in both samples, then it may be identified as being a genetic variation with a higher confidence.

In some embodiments, the sample may be cfDNA and the method may further comprise sequencing at least some of the same amplicons amplified from white blood cell DNA from the same subject. In these embodiments, the method may involve comparing the genetic variations called using cfDNA to the genetic variations called using the white blood cell DNA. If a variation is identified in both samples, then it may be identified as being a genetic variation with a lower confidence or not all. This embodiment provides a way to identify variations that may be potentially due to clonal hematopoiesis of indeterminate potential (CHIP) (see, generally, Funari et al, Blood 2016 128:3176 and Heuser et al, Dtsch Arztebl Int. 2016 113: 317-322), or may be germ line variants for example.

In alternative embodiments, the method may be performed by increasing or decreasing the threshold and/or cut-off for a particular sequence variation, without varying the number of replicate PCR reactions that amplify the variation. These embodiments, may comprise: (a) obtaining multiple pairs of primers that are compatible in a multiplex PCR reaction; (b) setting up at least two multiplex PCR reactions each containing different portions of the same sample, wherein the different reactions contain the same primers; (c) thermocycling the multiplex PCR reactions to produce multiple replicate amplicons; (d) sequencing the amplicons to produce sequence reads; (e) analyzing the sequence reads from replicate amplicons for a selected sequence variation to produce a score for the selected sequence variation, wherein the score: i. is based on the number of replicate amplicons that comprise a sequence variation that has a frequency above a cut-off; or ii. indicates the strength of the combined evidence for the sequence variation across the replicates; and (f) calling the sequence variation as a genetic variation based on the score, wherein the score and/or cut-off used for each selected sequence variation is based in part on: i. the expected frequency of the genetic variation, ii. the type cancer of the patient from which the sample was obtained, iii. treatment history of the patient from which the sample was obtained, iv. clinical significance of the genetic variation, v. previous tests undergone by the patient from which the sample was obtained, vi. the error profile of the genetic variation, vi. other genetic variations found in the sample, and/or vii the overall error rate of the sequencing, or any combination thereof. Details of how this alternative method may be performed may be adapted from other parts of this disclosure.

In some embodiments, the method may comprise providing a report indicating whether there are genetic variations in the sample, the type of genetic variation and/or an amino acid substitution caused by the genetic variation. In some embodiments, a report may additionally list approved (e.g., FDA approved) therapies for cancers that are associated with the genetic variation identified in the sample. This information can help in diagnosing a disease (e.g., whether the patient has cancer) and/or the treatment decisions made by a physician.

In some embodiments, the report may be in an electronic form, and the method comprises forwarding the report to a remote location, e.g., to a doctor or other medical professional to help identify a suitable course of action, e.g., to diagnose a subject or to identify a suitable therapy for the subject. The report may be used along with other metrics to determine whether the subject is susceptible to a therapy, for example.

In any embodiment, a report can be forwarded to a "remote location", where "remote location," means a location other than the location at which the sequences are analyzed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet, including email transmissions and information recorded on websites and the like. In certain embodiments, the report may be analyzed by an MD or other qualified medical professional, and a report based on the results of the analysis of the sequences may be forwarded to the patient from which the sample was obtained.

In some embodiments, a biological sample may be obtained from a patient, and the sample may be analyzed using the method. In particular embodiments, the method may be employed to identify and/or estimate the amount of variant copies of a genomic locus that are in a biological sample that contains both wild type copies of a genomic locus and variant copies of the genomic locus, where the variant copies have a sequence variation relative to the wild type copies of the genomic locus. In this example, the sample may contain at least 2 times, (e.g., at least 5 times, at least 10 times, at least 50 times, at least 100 times, at least 500 times, at least 1,000 times, at least 5,000 times or at least 10,000) more wild type copies of the genomic locus than variant copies of the genomic locus.

In some embodiments, the method does not involve shotgun sequencing an unenriched/unamplified sample, or sequencing the entire exome. Rather, the sequencing may be done as part of a larger sequencing effort that targets at least part of the coding sequences for up to 200, e.g., up to 100 or up to 50 genes, focusing on the coding sequences of AKT1, ALK, BRAF, CCND1, CDKN2A, CTNNB1, EGFR, ERBB2, ESR1, FGFR1, FGFR2, FGFR3, GATA3, GNA11, GNAQ GNAS, HRAS, IDH1, IDH2, KIT, KRAS, MAP2K1, MET, MYC, NFE2L2, NRAS, NTRK1, NTRK3, PDGFRA, PIK3CA, PPP2R1A, PTEN, ROS1, STK11, TP53 and U2AF1 as well as the coding sequences of other genes, mutations or which are associated with non-small cell lung cancer. In alternative embodiments, the method may be employed to detect oncogenic mutations in, e.g., PIK3CA, NRAS, KRAS, JAK2, HRAS, FGFR3, FGFR1, EGFR, CDK4, BRAF, RET, PGDFRA, KIT or ERBB2, which may be associated with breast cancer, melanoma, renal cancer, endometrial cancer, ovarian cancer, pancreatic cancer, leukemia, colorectal cancer, prostate cancer, mesothelioma, glioma, medulloblastoma, polycythemia, lymphoma, sarcoma or multiple myeloma (see, e.g., Chial 2008 Proto-oncogenes to oncogenes to cancer. Nature Education 1:1).

In some embodiments, a sample may be collected from a patient at a first location, e.g., in a clinical setting such as in a hospital or at a doctor's office, and the sample may be forwarded to a second location, e.g., a laboratory where it is processed and the above-described method is performed to generate a report. A "report" as described herein, is an electronic or tangible document which includes report elements that provide test results that may indicate the presence and/or quantity of minority variant(s) in the sample. Once generated, the report may be forwarded to another location (which may be the same location as the first location), where it may be interpreted by a health professional (e.g., a clinician, a laboratory technician, or a physician such as an oncologist, surgeon, pathologist or virologist), as part of a clinical decision.

The genetic variations identified by this method may be diagnostic, prognostic or theranostic.

In some embodiments, the method may be used to guide treatment decisions. In these embodiments, the method may be a method of treatment comprising performing or having performed the method described above, and administering a treatment to the patient if an actionable treatment is identified. Actionable mutations include, but are not limited to, activating mutations in EGFR and BRAF such as: G719X, exon19 deletions, V765A, T783A, V774A, S784P, L858R, S768I and L861X in EGFR and V600E; L601G; K601E; L597V/Q/R and G469V/S/R/E/A in BRAF. Actionable mutations also include rearrangements in ALK and ROS1, e.g., EML4-ALK, TFG-ALK, STRN-ALK, KIF5B-ALK, CD74-ROS1, SLC34A2-ROS1, SDC4-ROS1 and EZR-ROS1 fusions. For example, erlotinib (Tarceva), afatinib (Gilotrif), gefitinib (Iressa) or osimertinib (Tagrisso) may be administered to patients having an activating mutation in EGFR, crizotinib (Xalkori), ceritinib (Zykadia), alectinib (Alecensa) or brigatinib (Alunbrig) may be administered to patients having an ALK fusion, crizotinib (Xalkori), entrectinib (RXDX-101), lorlatinib (PF-06463922), crizotinib (Xalkori), entrectinib (RXDX-101), lorlatinib (PF-06463922), ropotrectinib (TPX-0005), DS-6051b, ceritinib, ensartinib or cabozantinib may be administered to patients having an ROS1fusion, and dabrafenib (Tafinlar) or trametinib (Mekinist) may be administered to patients having an activating mutation in BRAF. Many other actionable mutations, including mutations that can be used to guide treatment of a patient with an immune checkpoint inhibitor, are also known.

In other embodiments, the method may be used to monitor a treatment. For example, the method may comprise analyzing a sample obtained at a first timepoint using the method, and analyzing a sample obtained at a second time point by the method, and comparing the results, i.e., comparing which variations are called in the samples and the allele frequencies of the same. The first and second timepoints may be before and after a treatment, or two timepoints after treatment. For example, by comparing results obtained from one timepoint to another, the method may be used to identify new variations (e.g., mutations) that have appeared during the course of a treatment, or to determine if a previously identified variation is no longer present in the subject during the course of a treatment. The method can be used to determine whether the allele frequency of any mutations have changed (increased or decreased) during the course of the treatment. A patient's response to therapy can be monitored by detecting a change in either the allele frequency of mutations or in the presence of mutations. If multiple mutations are present, the allele frequency and allele frequency change can either be determined by combining the different mutations and replicates equally or alternatively they can be weighted for example based on likely clonality, clinical significance, probability of being a somatic change within the cancer as opposed to germline or CHIP and actionability. If a patient is determined to be likely responding to therapy, they may be kept on that therapy whilst if they are determined to be likely not responding they can be changed to an alternative therapy.

This method may also be used to determine if a subject is disease-free, or whether a disease is recurring.

In some embodiments, the method may be used for the analysis of minimal residual disease. In these embodiments, the primer pairs used in the method may be designed to amplify sequences that contain variations that have been previously identified in a patients tumor through either sequencing tumor material, cfDNA at an earlier time point or sequencing another suitable sample. The number of reactions containing each primer pair may be varied depending on, for example, whether the variant is predicted to be a driver mutation, the confidence with which the variant has been identified in the cancer, whether the variant is predicted to be clonal or subclonal in the cancer, whether the variant is located at a base that is typically noisy to sequence or not, whether the variant is in a region of the genome expected to be more or less fragmented (for example open or closed chromatin), the level of confidence that the variant is a somatic change present within the cancer rather than CHIP or a germ line change, if the type of variant is a point mutation or indel and if an indel if short or long. In some embodiments, the threshold for calling each variant can be increased or decreased based on whether the variant is predicted to be a driver mutation, whether the variant is predicted to be clonal or subclonal in the cancer, whether the variant is located at a base that is typically noisy to sequence or not for example. In some embodiments, the evidence for all the patient specific variants can be combined to determine whether the patient still has residual disease or may be disease free. The importance of each variant can be adjusted as described above.

As would be readily appreciated, many steps of the method, e.g., the sequence processing steps and the generation of a report indicating a genetic variation may be implemented on a computer. As such, in some embodiments, the method may comprise executing an algorithm that calculates the likelihood of whether a patient has a genetic variation based on the analysis of the sequence reads, and outputting the likelihood. In some embodiments, this method may comprise inputting the sequences into a computer and executing an algorithm that can calculate the likelihood using the input measurements.

As would be apparent, the computational steps described may be computer-implemented and, as such, instructions for performing the steps may be set forth as programing that may be recorded in a suitable physical computer readable storage medium. The sequencing reads may be analyzed computationally.

Any embodiment of the method described herein may be adapted to the analysis of bisulfite treated DNA. For example, the method could be adapted to detect epigenetic variations through bisulfite sequencing rather than genetic variations. In such an embodiment, bisulfite treated DNA would be analysed in replicate. PCR primers would be designed to amplify a range of CpG containing sites of interest. The number of replicates for each amplicon containing different CpG sites could be prioritised based on many criteria such the frequency with which a particular CpG site is expected to be hypermethylated or hypomethylated in the sample of interest, the significance of such hypo or hyper methylation and the level of noise expected when reading a particular CpG site. Again, as with variant calling the thresholds and cut-offs could also be adjusted for each CpG site based on factors such as these in order to call CpG sites either methylated or unmethylated and to determine the degree of DNA methylation.

What is claimed is:

1. A method for the analysis of minimal residual disease, the method comprising:
    (a) obtaining multiple pairs of primers, each pair designed to selectively amplify a plurality of sequence variations that have been previously identified in a patient's tumor, wherein the primer pairs are compatible in a multiplex amplification reaction;
    (b) performing a targeted multiplex amplification using the multiple pairs of primers to selectively amplify the plurality of sequence variations from cell-free DNA (cfDNA) isolated from a plasma sample obtained from the patient to produce amplicons;
    (c) sequencing the amplicons of step (b), or an amplification product thereof, thereby generating sequence reads for each of the plurality of sequence variations, wherein for each sequence variation, the sequence reads comprise a majority of wild type sequences and a minority of sequences containing the identified sequence variations;
    (d) calculating a score based on the minority of sequences containing the identified sequence variations, wherein the score is calculated by combining evidence from the minority of sequences containing the plurality of sequence variations; and
    (e) using the calculated score of step (d) to determine the presence or absence of minimal residual disease in the patient, wherein the determination of minimal residual disease is indicative of cancerous cells remaining in the patient.

2. The method of claim 1, wherein the multiple pairs of primers comprise at least 10 pairs of primers.

3. The method of claim 1, wherein performing a targeted multiplex amplification further comprises performing at least two replicate targeted multiplex amplifications.

4. The method of claim 3, wherein combining evidence from the minority of sequences for the plurality of sequence variations further comprises combining evidence from the minority of sequences for the plurality of sequence variations from each replicate targeted multiplex amplification.

5. The method of claim 1, wherein the minority of sequences containing a sequence variation is less than 0.5% of the sequence reads.

6. The method of claim 1, wherein the minority of sequences containing a sequence variation is between 0.001% and 0.01% of the sequence reads.

7. The method of claim 1, wherein the determining whether the patient has minimal residual disease of step (e) comprises comparing the score to a threshold value.

8. The method of claim 7, wherein the threshold value varies based on the number of sequence reads produced in step (c).

9. The method of claim 7, wherein the threshold value is based on an error distribution that indicates how often a sequence variation may be observed due to amplification and/or sequencing error.

10. The method of claim 9, wherein the threshold value is determined using a binomial, overdispersed binomial, beta, normal, exponential, or gamma probability distribution model based on sequencing of control samples.

11. The method of claim 9, wherein the threshold value is based on an error distribution calculated for each of the plurality of sequence variations.

12. The method of claim 1, wherein the score is an estimated allele frequency for the plasma sample based on the minority of sequences for the plurality of sequence variations.

13. The method of claim 1, wherein the plurality of sequence variations comprise clonal variations.

14. The method of claim 1, further comprising performing a second multiplex amplification of the amplicons of step (b), wherein the second multiplex amplification uses primer pairs that provide compatibility with a sequencing platform.

15. The method of claim 14, wherein the sequencing platform is selected from the group consisting of a reversible terminator method, a pyrosequencing method, a sequencing by ligation method, and a fluorescent base-cleavage method.

16. A method for the analysis of minimal residual disease, the method comprising:
    (a) obtaining multiple pairs of primers designed to amplify a plurality of sequence variations that are associated with cancer, wherein the primer pairs are compatible in a multiplex amplification reaction;
    (b) performing a targeted multiplex amplification using the multiple pairs of primers to amplify the plurality of sequence variations from cell-free DNA (cfDNA) isolated from a plasma sample of a patient to obtain amplicons;
    (c) sequencing the amplicons of step (b), or an amplification product thereof, to produce sequence reads for the plurality of sequence variations, wherein for each sequence variation, the sequence reads comprise a majority of wild type sequences and a minority of sequences containing the sequence variations;
    (d) calculating a score based on the minority of sequences containing the sequence variations, wherein the score is calculated by combining evidence from the minority of sequences for the plurality of sequence variations; and
    (e) determining, based on the score, whether the patient has minimal residual disease.

17. The method of claim 16, wherein the plurality of sequence variations comprise oncogenic mutations.

18. The method of claim 16, wherein the plurality of sequence variations are previously identified in a tumor tissue sample from the patient.

19. The method of claim 16, further comprising providing a report indicating whether the patient has minimal residual disease.

20. The method of claim 16, further comprising performing steps (b)-(e) of the method on a second, subsequent plasma sample from the patient, and comparing the score for the plasma sample and the second, subsequent plasma sample to determine whether the patient has minimal residual disease.

* * * * *